United States Patent [19]

Pelosi, Jr.

[11] 4,021,444

[45] May 3, 1977

[54] 2-[5-(3,4-DIMETHOXYPHENYL)-2-FURYL-]IMIDAZOLINE HYDROCHLORIDE

[75] Inventor: Stanford S. Pelosi, Jr., Norwich, N.Y.

[73] Assignee: Morton-Norwich Products, Inc., Norwich, N.Y.

[22] Filed: May 10, 1976

[21] Appl. No.: 684,722

[52] U.S. Cl. .......................... 260/309.6; 260/347.7; 424/273

[51] Int. Cl.² ...................................... C07D 405/04

[58] Field of Search ................................. 260/309.6

[56] References Cited

UNITED STATES PATENTS

| | | | |
|---|---|---|---|
| 1,999,989 | 4/1935 | Bockmühl et al. | 260/309.6 |
| 2,457,047 | 12/1948 | Kyrides et al. | 260/309.6 |
| 3,277,112 | 10/1966 | Bencze | 260/309.6 |
| 3,850,926 | 11/1974 | Stähle et al. | 260/309.6 |
| 3,927,023 | 12/1975 | Brown et al. | 260/309.6 |

OTHER PUBLICATIONS

Kelarev et al. Chem. Abst. 1974, vol. 80, No. 37039x.
Kempter et al. Chem. Abst. 1972, vol. 76, No. 99557r.
Schubert et al. Chem. Abst. 1963, vol. 58, cols. 2445–2446.
Tanaseichuk et al. Chem. Abst. 1973, vol. 78, No. 43366b.

*Primary Examiner*—Natalie Trousof
*Attorney, Agent, or Firm*—Anthony J. Franze

[57] ABSTRACT

2-[5-(3,4-Dimethoxyphenyl)-2-furyl]imidazoline hydrochloride is useful as an anti-inflammatory agent.

1 Claim, No Drawings

2-[5-(3,4-DIMETHOXYPHENYL)-2-FURYL-]IMIDAZOLINE HYDROCHLORIDE

This invention relates to the compound 2-[5-(3,4-dimethoxyphenyl)-2-furyl]imidazoline hydrochloride of the formula:

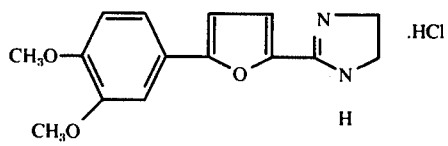

This compound possesses pharmacologic activity. It is particularly useful as an anti-inflammatory agent as evidenced by its ability to inhibit edema induced in rats by the administration of carrageenin. Thus, when administered at a dose of 300 mg/kg suspended in a vehicle such as aqueous methyl cellulose per os to rats receiving carrageenin, edema associated with that substance is inhibited [Winter et al., P.S.E.B.M. 114:544 (1964)].

This compound is preferably prepared in accordance with the following example:

To 248 g (1.3 m) of 3,4-dimethoxyaniline hydrochloride in 1 liter of water was added 300 ml of concentrated HCl. After cooling to −5°–0°, a solution of 91 g (1.3 m) of sodium nitrite in 300 ml of water was added in about 1 hr while maintaining the temperature at −5°–2°. After further stirring at the same temperature range for 1½ hr, 210 g of solid sodium acetate was added to adjust the pH to ca. 3.5. Then a solution of 72 g of cupric chloride dihydrate in 400 ml of water and 252 g (2.6 m) of furfural in 500 ml of water was added. The mixture was allowed to stir for 8 days and then extracted with toluene. The toluene extract was washed with water and dried over $MgSO_4$. After filtering off $MgSO_4$, the toluene filtrate was concentrated in a water bath at reduced pressure. The excess furfural was also distilled off in a boiling water bath at reduced pressure. A dark viscous liquid residue weighing 292 g was obtained.

Part of the above dark viscous liquid (287 g) was stirred with 4 liter of SDA-32 and filtered. The filtrate was concentrated to half of its original volume and then heated at reflux with 172 g (2.48 m) of hydroxylamine hydrochloride and 202 g (2.48 m) of anhydrous sodium acetate in 400 ml of water. After 4 hr of reflux, the mixture was allowed to cool slightly and then poured onto crushed ice. Gummy material separated at first and gradually solidified on standing. The solid was collected, washed well with water and air dried. The yield was 156 g. Recrystallization from a 50/50 mixture of isopropanol/$H_2O$ gave, in two crops, 70.5 g (22%) of 5-(3,4-dimethoxyphenyl)-2-furaldehyde oxime. An analytical sample melted at 140°–142°.

A mixture of 70.5 g (0.29 m) of the above oxime in 650 ml of acetic anhydride was heated at reflux for 3 hr. After slight cooling, the solution was poured onto crushed ice with stirring in a 4 liter beaker. The solid was collected, washed well with water and air dried. The yield was 49.3 g (77.5%). Recrystallization of 45 g from 1.8 liter of SDA-32 gave 37 g of dark brown crystalline 5-(3,4-dimethoxyphenyl)-2-furonitrile. An analytical sample melted at 151°–153°.

Into a mixture of the recrystallized 5-(3,4-dimethoxyphenyl)-2-furonitrile (20 g) in 500 ml of absolute ethanol was bubbled HCl gas for 2 hr with some cooling. The mixture was filtered and the green solid was washed with some anhydrous ether and dried in a vacuum desiccator. Two more crops were obtained by addition of ether to the filtrate. Total yield was 24 g (86%) of ethyl 5-(3,4-dimethoxyphenyl)-2-furimidate hydrochloride.

A mixture of 51 g (0.16 mole) of ethyl 5-(3,4-dimethoxyphenyl)-2-furimidate hydrochloride, 11 g (0.18 mole) of ethylenediamine, and 850 ml of absolute ethanol was refluxed for 5 hrs and then kept overnight at room temperature. The solid was recrystallized from acetic acid, washed with ether, and air dried to yield 33 g (65%) of 2-[5-(3,4-dimethoxyphenyl)-2-furyl]imidazoline hydrochloride. An analytical sample was prepared by recrystallizing a sample from methanol and drying in the vacuum pistol at the temperature of refluxing $CHCl_3$, m.p. 291°–293°.

Anal. Calcd. for $C_{15}H_{16}N_2O_3$. HCl: C, 58.35; H, 5.55; N, 9.07

Found: C, 58.09; H, 5.79; N, 8.98

What is claimed is:

1. The compound 2-[5-(3,4-dimethoxyphenyl-2-furyl]imidazoline hydrochloride.

* * * * *